US000001137H

United States Statutory Invention Registration [19]

[11] Reg. Number: H1137

Easter et al. [43] Published: Feb. 2, 1993

[54] WAFER BONDING TECHNIQUE FOR DIELECTRIC ISOLATION PROCESSING

[75] Inventors: William G. Easter, Reading; Richard H. Shanaman, III, Myerstown, both of Pa.

[73] Assignee: American Telephone and Telegraph Company, New York, N.Y.

[21] Appl. No.: 608,955

[22] Filed: Nov. 5, 1990

[51] Int. Cl.[5] ..... G01N 33/18

[52] U.S. Cl. ..... 437/62; 437/34; 437/56; 437/228

[58] Field of Search ..... 437/62, 86, 974; 148/DIG. 12, DIG. 135

[56] References Cited

U.S. PATENT DOCUMENTS

| | | | |
|---|---|---|---|
| 4,700,466 | 10/1987 | Nakagawa et al. | 437/247 |
| 4,774,196 | 9/1988 | Blanchard | 437/24 |
| 4,826,787 | 5/1989 | Muto et al. | 437/208 |
| 4,851,078 | 7/1989 | Short et al. | 156/632 |
| 4,851,366 | 7/1989 | Blanchard | 437/61 |
| 4,854,986 | 8/1989 | Raby | 156/87 |
| 4,878,957 | 11/1989 | Yamaguchi et al. | 148/33.3 |
| 4,883,215 | 11/1989 | Goesele et al. | 228/116 |
| 4,970,175 | 11/1990 | Haisma et al. | 437/90 |
| 5,013,681 | 5/1991 | Godbey et al. | 437/86 |

FOREIGN PATENT DOCUMENTS

| | | | |
|---|---|---|---|
| 63-56936 | 3/1988 | Japan | 148/DIG. 135 |
| 63-62252 | 3/1988 | Japan | 437/86 |
| 63-126245 | 5/1988 | Japan | 437/62 |
| 1012544 | 1/1989 | Japan | 148/DIG. 135 |
| 2044749 | 2/1990 | Japan | 437/86 |
| 2067746 | 3/1990 | Japan | 148/DIG. 135 |

OTHER PUBLICATIONS

Wolf et al., "Silicon Processing for the VLSI ERA", Lattice Press, Sunset Beach, CA., pp. 191–195.

"Silicon Wafer-Bonding Process Technology . . . ", T. Abe et al., Tech., May 6–11, 1990.

*Primary Examiner*—Robert L. Stoll
*Assistant Examiner*—Joseph D. Anthony
*Attorney, Agent, or Firm*—Wendy W. Koba

[57] ABSTRACT

A process for forming a dielectrically isolated wafer is disclosed. In particular, the conventional process is altered to replace the step of growing the thick polysilicon handle layer with the steps of growing a relatively thin conformal coating layer and bonding a single crystal wafer thereto. The wafer will become the substrate of the final device structure. The process of bonding is considered to be more efficient and economical than the prior art polysilicon growth process. Additionally, the tub structures of the wafer bonding process may be exposed to a somewhat lower temperature (for bonding) for shorter period of time than the tub regions of the conventional thick polysilicon DI structures. Therefore, the tub regions will exhibit superior qualities (e.g., less stress, fewer crystal defects) when compared with those formed with the conventional polysilicon growth technique. The wafer bonding process may be utilized with virtually and tub structure since the bonding step occurs subsequent to any tub fabrication processes.

15 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

H001137

WAFER BONDING TECHNIQUE FOR DIELECTRIC ISOLATION PROCESSING

BACKGROUND OF THE INVENTION

1. Technical Field

The present invention relates to a dielectric isolation processing techniques for integrated circuits and, more particularly, to the utilization of a wafer bonding process in the fabrication of dielectrically isolated wafers.

2. Description of the Prior Art

Dielectric isolation (DI) has been used extensively in integrated circuit technology for fabricating high voltage devices which require a relatively large degree of inter-device isolation. In general, the DI process involves etching grooves in a silicon substrate (the grooves delineating the boundaries of the DI regions, often referred to as "tubs"). The etched substrate is then oxidized to form a layer sufficiently thick so as to provide the desired isolation. A relatively thick polysilicon layer, or "handle" is subsequently grown over the oxide. The structure is then inverted and the exposed bottom of the silicon substrate is ground and polished away until the surface of the tub regions is exposed. The polysilicon handle then forms the "substrate" of the final structure. U.S. Pat. No. 4,820,653 issued to W. G. Easter et al. on Apr. 11, 1989 describes in detail the DI process as outlined above. A problem with the conventional DI technique is that the process of growing a thick polysilicon handle is both time-consuming and expensive. Further, the prolonged exposure of the tub regions to the elevated temperature required for polysilicon deposition has been found to degrade the quality of the tub regions themselves. The grown polysilicon handle forms the "substrate" of the final device structure and is inherently of poorer quality (i.e., higher defect density, stress) than a monocrystalline silicon substrate.

An alternative isolation technique, referred to as Silicon On Insulator (SOI) utilizes wafer bonding and a buried oxide layer to provide inter-device isolation. Simply, a first silicon substrate is oxidized over a surface region and a second substrate is bonded to the oxide layer of the first substrate. There exist many different techniques, usually involving heat treatments, to bond the wafers together. An article entitled "Silicon Wafer-Bonding Process Technology for SOI Structures", by T. Abe et al. appearing in "Proceedings of 4*th Int. Symp. on Silicon-on-Insulator Technology and Devices,* May 1990 describes in detail various aspects of the SOI technology. Alone, however, SOI cannot provide inter-device isolation for devices fully contained within the same substrate.

U.S. Pat. No. 4,851,078 issued to J. P. Short et al. on Jul. 28, 1989 utilizes a combination of the above-described processes to form a dielectrically isolated silicon-on-insulator semiconductor device. The Short et al. process, however, requires at least two full wafer bonding sequences of operations (e.g., the bonding together of a series of three wafers) to form the final device structure.

A need remains in the prior art, therefore, for a relatively simple DI process technique which addresses the various limitations described above.

SUMMARY OF THE INVENTION

The need remaining in the prior art is solved in accordance with the present invention which relates to a DI fabrication process and, more particularly, to a DI process which includes a wafer bonding step to improve the quality of the final device structure.

In accordance with one embodiment of the present invention, a conventional DI fabrication process is altered such that the step of growing the thick polysilicon "handle" is replaced by the steps of: (1) growing a relatively thin conformal coating layer (so as to fill the exposed grooves); and (2) bonding a silicon wafer to the planarized surface of the thin conformal layer. Polysilicon, silicon nitride, or various other suitable materials may be used as the conformal coating. As with the conventional DI process, the bonded structure is then inverted and the original substrate removed to expose the tub portions. The inventive device, however, will include as the final substrate single crystal silicon (the bonded wafer), instead of the polysilicon handle of the prior art.

In accordance with an alternative method, the relatively thin conformal layer may be further planarized so as to expose the underlying electrically insulative layer. The second silicon wafer is then bonded to both the exposed insulator and remaining conformal coating.

The DI wafer information technique of the present invention may be modified to include any desired variations to the DI tubs themselves, since the wafer bonding step occurs subsequent to all tub processing. In particular, a bonded DI wafer formed in accordance with the present invention may include tubs with different conductivity types (i.e., complementary tubs for CMOS devices), buried diffusion regions, wrap-around regions, and/or buried silicide layers, for example.

An advantage of the wafer bonding technique of the present invention is that the bonding process itself is considerably less time consuming than the conventional prior art process of growing a thick polysilicon "handle" substrate. Further, the bonding operation may take place at a lower temperation than the prior art polysilicon deposition process. The decrease in both the exposure time and temperature results in providing tub regions of improved quality (e.g., less stress, fewer crystal defects) than those of the prior art. The shorter time period also allows for relatively shallow tub regions to be used, since less out-diffusion of the various dopants within the tub regions will occur.

Other and further variations of the present invention will become apparent during the course of the following discussion and by reference to the accompanying drawings.

BRIEF DESCRIPTION OF THE DRAWING

Referring now to the drawings, where like numerals represent like parts in several views.

DETAILED DESCRIPTION

FIGS. 1–7 illustrate an exemplary wafer bonded dielectric isolation (DI) fabrication process of the present invention. Although the structure, as illustrated, shows the fabrication of a single DI region, it is to be understood that the wafer bonding technique of the present invention is utilized to simultaneously form a large number of such regions within the wafer structure.

Figure 1:
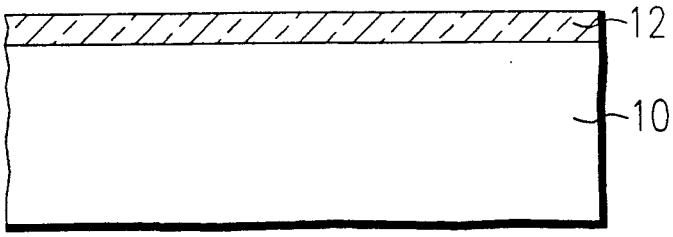
FIGS. 1–7 illustrate an exemplary wafer bonding dielectric isolation fabrication process of the present invention.
Figure 2:
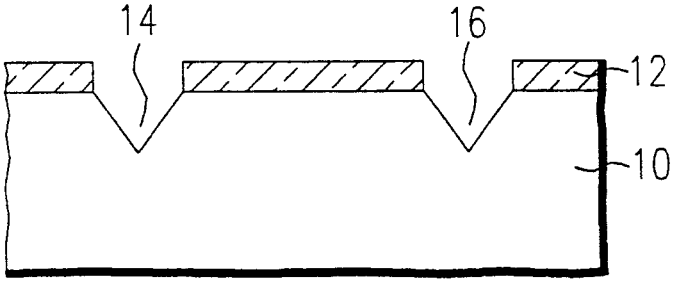
Figure 3:
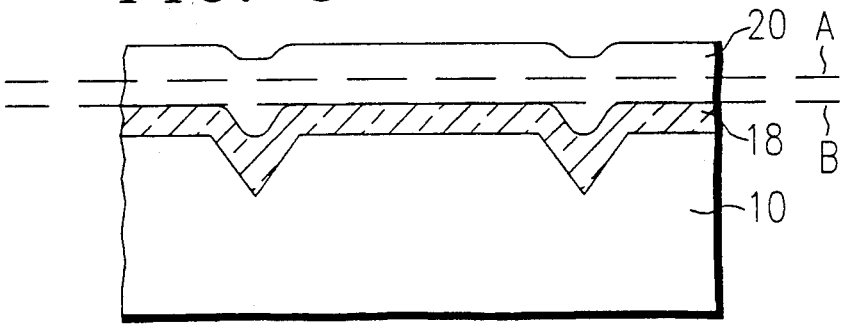
Figure 4:
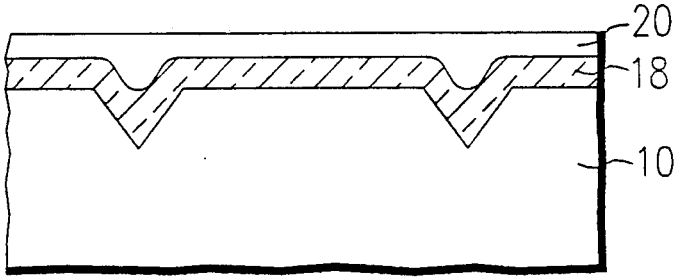
Figure 5:
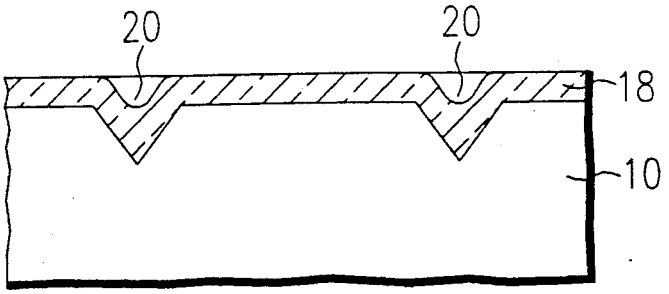

An initial monocrystalline silicon wafer 10 is provided with a patterning layer 12 (for example, oxide) as illustrated in FIG. 1. Layer 12 is patterned to delineate the locations of the desired tub regions. The structure is subsequently etched using conventional techniques to form, as shown in FIG. 2, a pair of grooves 14, 16. Although illustrated as V-grooves, it is to be understood that various other groove geometries are possible and are not considered to be a limiting factor in practicing the techniques of the present invention. An oxide layer 18 and conformal coating layer 20 are then formed, in sequence, over the etched surface of substrate 10. Layer 18 is formed to comprise a thickness sufficient for providing the desired electrical isolation between the various devices in the final structure (for example, 10,000 Å). Conformal coating layer 20 is relatively thin, approximately at least twice the tub depth (i.e., sufficient to at least fill grooves 14, 16. Conformal layer 20 may then planarized, as indicated by dotted line A in FIG. 3, to form the structure as depicted in FIG. 4. As shown in FIG. 4, a portion of layer 20 remains such that the underlying oxide 18 is fully covered. Alternatively, the structure of FIG. 3 may be planarized down to dotted line B, forming the structure of FIG. 5. In this embodiment, oxide 18 is exposed and only that portion of conformal layer 20 utilized to fill the voids created by grooves 14, 16 remains. The planarization in either case may be accomplished with a conventional grinding and/or polishing procedure. As mentioned above, polysilicon (LPCVD deposited, for example) or silicon nitride may be used to form conformal layer 20.

Figure 6:
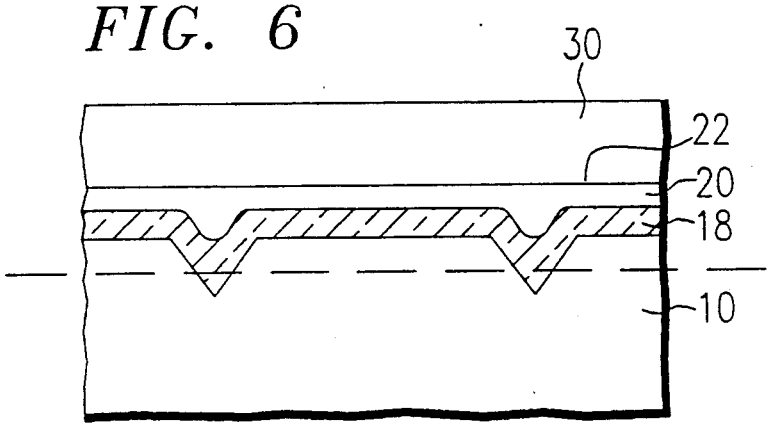

The wafer bonding portion of the inventive process occurs at this point in time, where a second silicon wafer 30 is bonded to top surface 22 of conformal layer 20 (or alternatively, to the exposed surface of oxide 18 and conformal layer 20), as shown in FIG. 6. The bonding may be accomplished, for example, by bringing wafer 30 into contact with surface 22 with a force sufficient to provide adhesion. The adhered structure may then be annealed for a time and at a temperature sufficient to form a permanent bond therebetween. For example, an anneal for approximately two to four hours at a temperature of approximately 1000° C. has been found sufficient in experimentation.

Figure 7:
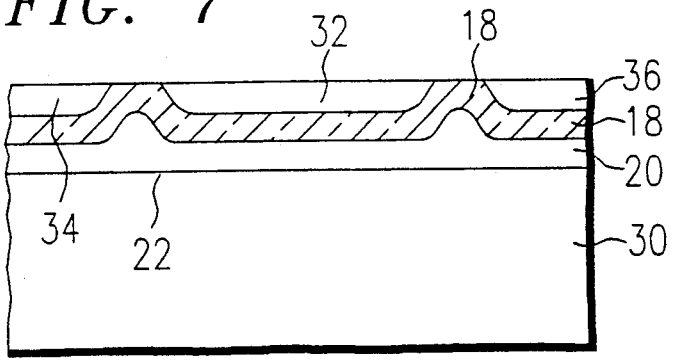

The final DI structure is formed by removing substrate 10, as indicated by the dotted line in FIG. 6. The removal may be accomplished by any of the grinding, etching and/or polishing operations conventionally used in the DI process to form the final structure. FIG. 7 illustrates the final DI structure as formed in accordance with the present invention, where monocrystalline silicon substrate 30 is utilized as the substrate of the final structure. As shown, the inverted grooves 14, 16 result in the formation of a tub region 32, which is isolated by oxide layer 18 from the neighboring tub regions 34, 36.

As mentioned above, the inventive process of wafer bonding is considerably less time-consuming than the prior art polysilicon deposition process (i.e., approximately one hour to grow a 10–40 μm of thin polysilicon (i.e., layer 20) versus at least three hours to grow 500–600 μm of thick polysilicon for conventional DI wafers). The temperature for deposition may also be reduced accordingly, from a nominal of 1250° C. for thick polysilicon, to approximately 1000° C. for an exemplary thin polysilicon layer used in the structure of the present invention. The reductions in time and temperature result in less diffusion within the tub, therefore, the tub dimensions may be scaled down with respect to prior art designs. For example, a 4:1 reduction may be achieved such that conventional 20 μm tub depths may be replaced by 5 μm tubs in the inventive wafer bonding structure. Further, reducing the exposure time of the tub material to the elevated temperatures required for thick polysilicon growth has been found to reduce the stress within the tub regions, resulting in fewer crystal defects. The time reduction is especially beneficial in tub structures of the form p-conductivity with a $p^+$-type wrap-around layer, since any prolonged heat treatment (as is used with the conventional polysilicon growth) results in excessive boron diffusion from the wrap-around into the tub, thus detrimentally increasing the thickness of the wrap-around layer. An additional advantage of the wafer bonding process of the present invention is that relatively large wafers (e.g., 125–150 mm) may be formed. With the conventional DI process of the prior art, the ability to grow a thick polysilicon handle over such a large area was extremely limited. Therefore, the bonding technique of the present invention may increase throughput not only in terms of providing a faster process, but also in the fact that larger wafers may be utilized.

Figure 8:
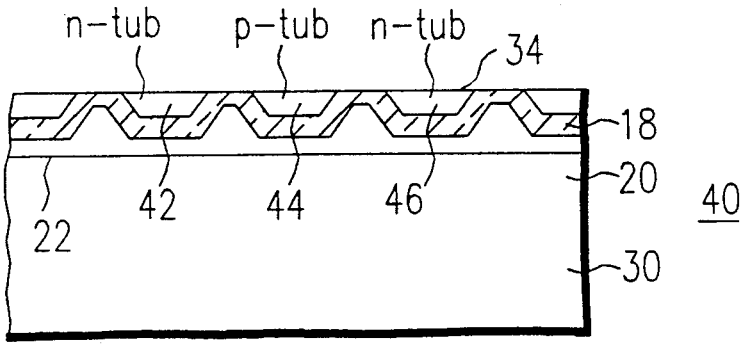
FIGS. 8–10 illustrates various dielectrically isolated structures including a silicon wafer bonded substrate formed in accordance with the teachings of the present invention.
Figure 9:
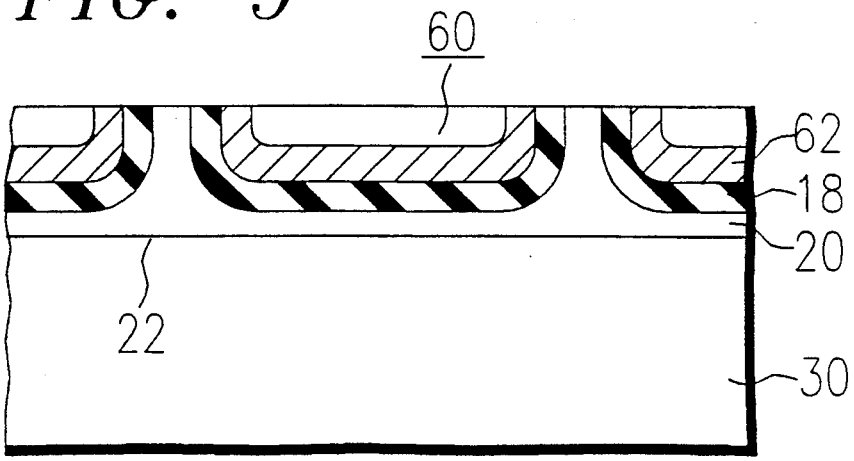
Figure 10:
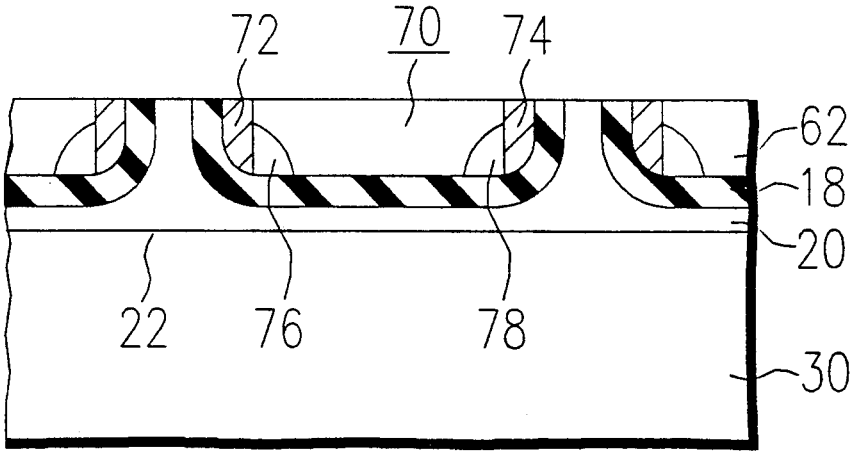

As mentioned above, the wafer bonding technique of the present invention may be utilized with various DI tub structures, since the bonding operation occurs subsequent to the tub formation process. FIGS. 8–10 illustrate various tub structures which may be formed to include the bonded wafer substrate of the present invention. In particular, the structure of FIG. 8 includes a DI wafer 40 with tub regions 42, 44, 46 of various conductivities and of complementary types (i.e., both n-type and p-type tubs formed within the same wafer). An exemplary technique for forming such tub types in disclosed in U.S. Pat. No. 4,820,653 assigned to the assignee of record and herein incorporated by reference. As shown, wafer 40 includes a relatively thin polysilicon layer 20 underlying the plurality of tub regions 42,44,46 and a bonded monocrystalline silicon substrate 30.

A tub structure 60 including a buried silicon layer 62 formed in accordance with the teachings of the present invention is illustrated in FIG. 9. As shown, thin polysilicon layer 20 is formed at the tub boundary insulation layer 18, with monocrystalline substrate 30 bonded to surface 22 of layer 20. Tube structure 70 illustrated in FIG. 10 includes a pair of silicide sidewalls 72, 74 and buried diffusion regions 76,78. As shown, tub 70 is surrounded by oxide layer 18 and is disposed above polysilicon layer 20 and bonded substrate 30. The substructures as illustrated in FIGS. 9 and 10 are disclosed and described in detail in U.S. Pat. No. 4,839,309 also issued to the assignee of record and herein incorporated by reference.

It is to be understood that the various DI embodiments illustrated in the associated drawings are exemplary only, and the wafer bonding technique of the present invention can be utilized with various other tub arrangements which would be apparent to those of ordinary skill in the art.

We claim:

1. In a method of forming a dielectrically isolated wafer, replacing the step of growing a polysilicon handle layer with the following steps:

a) forming a layer of conformal material of a thickness sufficient to fill any voids on the wafer surface;

b) planarizing the conformal layer of step a);

c) bonding a silicon substrate to the planarized layer of step b).

2. In the method of claim 1, when performing step b), planarizing the conformal layer until an underlying dielectric layer is exposed.

3. In the method of claim 1, when performing step b), planarizing the conformal layer such that an underlying dielectric layer is not exposed.

4. In the method of claim 1, when performing step c), utilizing the following steps:

$c_1$) attaching a silicon substrate to the planarized conformal layer with a force sufficient to cause adhesion; and $c_2$) heating the adhered structure for a time and at a temperature sufficient to form a permanent bond.

5. In the method of claim 4, when performing step $c_2$, heating the structure for at least two hours at a temperature of approximately 1000° C.

6. In the method of claim 1, when performing step a), growing a polysilicon layer.

7. In the method of claim 6, growing a polysilicon layer of a thickness at least twice that of an associated tub region.

8. In the method of claim 1, when performing step a), forming a silicon nitride layer.

9. A method of forming a dielectrically isolated structure, the method comprising the steps of:

a) providing a first silicon substrate;

b) etching said first substrate to delineate locations of predetermined tub regions;

c) forming a dielectric layer over the etched surface formed in step b) to form a dielectric layer sufficient to provide electrical isolation in the final dielectrically isolated structure;

d) forming a conformal layer over the dielectric layer of step c), the conformal layer being of a thickness sufficient to at least fill the etched tub regions;

e) bonding a second silicon substrate to the planarized conformal layer of step d); and f) removing a portion of the first silicon substrate sufficient to expose the tub region.

10. The method of claim 9 wherein in performing step d), the conformal layer is planarized.

11. The method of claim 10 wherein the conformal layer is planarized until the underlying dielectric layer is exposed.

12. The method of claim 9 wherein in performing step e), the following steps are performed:

$e_1$) attaching the second silicon substrate to the conformal layer with a force sufficient to cause adhesion; and $e_2$) heating the adhered structure for a time and at a temperature sufficient to form a permanent bond therebetween.

13. The method of claim 12 wherein in performing step $e_2$, heating the structure for at least two hours at a temperature of approximately 1000° C.

14. The method of claim 9 wherein in performing step d), a polysilicon layer is formed.

15. The method of claim 9 wherein in performing step d), a silicon nitride layer is formed.

* * * * *